US00PP34642P3

(12) United States Plant Patent
Post

(10) Patent No.: US PP34,642 P3
(45) Date of Patent: Oct. 11, 2022

(54) ***CHRYSANTHEMUM* PLANT NAMED 'DLFSHOR12'**

(50) Latin Name: ***Chrysanthemum* X *morifolium***
Varietal Denomination: DLFSHOR12

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/503,098

(22) Filed: Oct. 15, 2021

(65) Prior Publication Data

US 2022/0124955 P1 Apr. 21, 2022

Related U.S. Application Data

(60) Provisional application No. 63/093,198, filed on Oct. 17, 2020.

(51) Int. Cl.
*A01H 5/02* (2018.01)
*A01H 6/14* (2018.01)

(52) U.S. Cl.
USPC ..... Plt./287
CPC ..... *A01H 6/1424* (2018.05)

(58) Field of Classification Search
USPC ..... Plt./287, 288, 291
CPC ... A01H 5/02; A01H 5/00; A01H 6/14; A01H 6/1424
See application file for complete search history.

(56) References Cited

PUBLICATIONS

Deliflor Delishow 2019, retrieved on Jan. 12, 2022, retrieved from the Internet at https://www.deliflor.nl/15579/Delishow-2019, 2 pp. (Year: 2019).*
Upov Pluto 20220108, retrieved on Jan. 12, 2022, retrieved from the Internet at https://pluto.upov.int/result, one page. (Year: 2022).*

* cited by examiner

*Primary Examiner* — June Hwu
(74) *Attorney, Agent, or Firm* — C. Anne Whealy

(57) ABSTRACT

A new and distinct cultivar of *Chrysanthemum* plant named 'DLFSHOR12', characterized by its upright plant habit; uniform growth habit; dark green-colored leaves; uniform and freely flowering habit; strong upright flowering stems; decorative-type inflorescences with white and reddish purple bi-colored ray florets; resistance to *Fusarium*; relative tolerance to high and low temperatures; and good postproduction longevity.

1 Drawing Sheet

Figure 1:
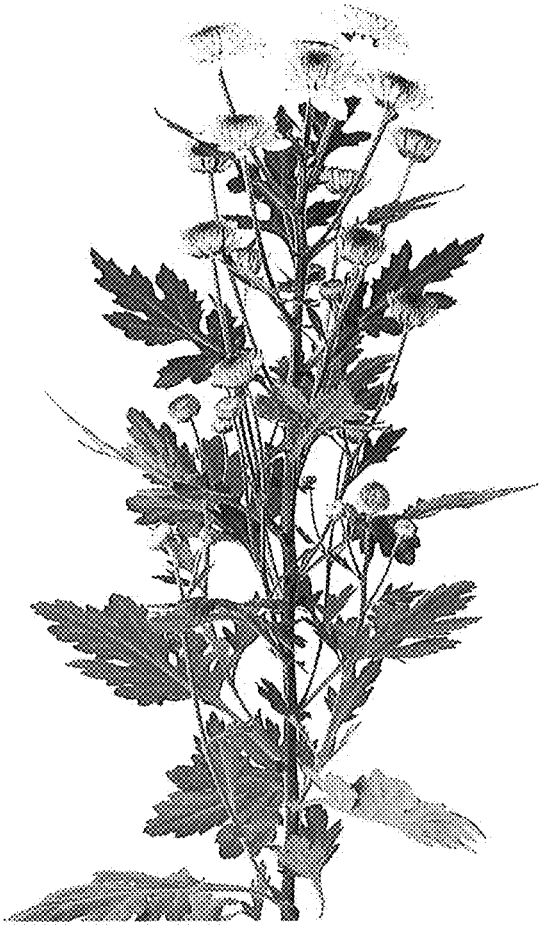

Botanical designation: *Chrysanthemum* X *morifolium*.
Cultivar denomination: 'DLFSHOR12'.

STATEMENT REGARDING PRIOR DISCLOSURES BY INVENTOR/APPLICANT & ASSIGNEE

A Colombian Plant Breeders' Rights application for the instant plant was filed by the Assignee, Deliflor Royalties B.V. of Maasdijk, The Netherlands on Aug. 2, 2020, application number A202701. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFSHOR12'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in October, 2013 of a proprietary selection of *Chrysanthemum* x *morifolium* identified as code number DB 45763, not patented, as the female, or seed, parent with a proprietary selection of *Chrysanthemum* x *morifolium* identified as code number DB 33592, not patented, as the male, or pollen, parent. The new *Chrysanthemum* plant was discovered and selected as a single flowering plant from within the progeny of the stated cross-pollination in a controlled greenhouse environment in Maasdijk, The Netherlands in May, 2015.

Asexual reproduction of the new *Chrysanthemum* plant by vegetative terminal cuttings since May, 2015 in a controlled greenhouse environment in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFSHOR12'. These characteristics in combination distinguish 'DLFSHOR12' as a new and distinct *Chrysanthemum* plant:

1. Upright plant habit; uniform growth habit.
2. Dark green-colored leaves.
3. Uniform and freely flowering habit.
4. Strong upright flowering stems.
5. Decorative-type inflorescences with white and reddish purple bi-colored ray florets.
6. Resistant to *Fusarium* (*Fusarium oxysporum*).
7. Relatively tolerant to high and low temperatures.
8. Good postproduction longevity.

Plants of the new *Chrysanthemum* differ primarily from plants of the female parent selection in ray floret color as ray florets of plants of the new *Chrysanthemum* are white and reddish purple bi-colored whereas ray florets of plants of the female parent selection are white in color. In addition, plants of the new *Chrysanthemum* have larger inflorescences than plants of the female parent selection.

Plants of the new *Chrysanthemum* differ primarily from plants of the male parent selection in ray floret color as ray florets of plants of the new *Chrysanthemum* are white and reddish purple bi-colored whereas ray florets of plants of the male parent selection are pale purple and reddish purple in color. In addition, plants of the new *Chrysanthemum* have slightly smaller inflorescences than plants of the male parent selection.

Plants of the new *Chrysanthemum* can also be compared to plants of *Chrysanthemum* X *morifolium* 'DLFABB12', disclosed in U.S. Plant Pat. No. 32,006. In side-by-side comparisons, plants of the new *Chrysanthemum* differ primarily from plants of 'DLFABB12' in the following characteristics:

1. Developed ray florets of plants of the new *Chrysanthemum* are white and reddish purple in color whereas developed ray florets of plants of 'DLFABB12' are mostly white in color.
2. Ray florets of plants of the new *Chrysanthemum* have emarginate apices whereas ray florets of plants of 'DLFABB12' have rounded apices.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph at the top of the sheet (FIG. 1) comprises a side perspective view of a typical flowering stem of 'DLFSHOR12' grown as a spray-type cut flower.

Figure 2:
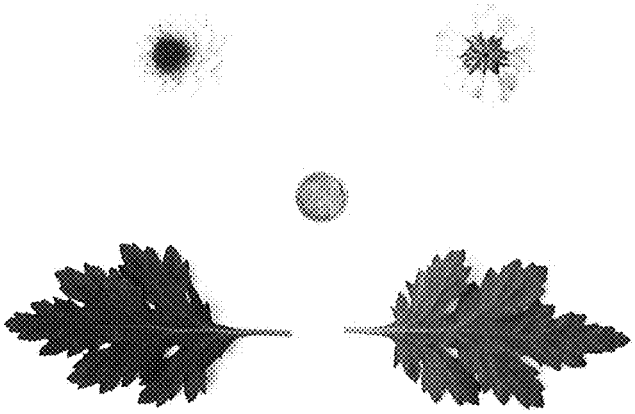

The photograph at the bottom of the sheet (FIG. 2) is a close-up view of upper (left) and lower (right) surfaces of typical inflorescences (top of figure) and typical leaves (bottom of figure) of 'DLFSHOR12'.

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFSHOR12'.

Parentage:

*Female, or seed, parent*.—Proprietary selection of *Chrysanthemum* x *morifolium* identified as code number DB 45763, not patented.

*Male, or pollen, parent*.—Proprietary selection of *Chrysanthemum* x *morifolium* identified as code number DB 33592, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 65.2 cm.

*Plant height, soil level to top of inflorescence plane*.—About 69.7 cm.

*Plant (spray) diameter*.—About 24.7 cm.

*Flowering stem length*.—About 60.7 cm.

*Flowering stem diameter*.—About 7 mm.

*Flowering stem internode length*.—About 3.2 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 143A.

*Flowering stem color, developed*.—Close to 146B and 147B.

*Leaf description*.—Arrangement: Alternate; simple. Length: About 12.9 cm. Width: About 9 cm. Shape, in overall outline: Broadly ovate. Apex: Abruptly acute, minute. Base: Attenuate. Margin: Palmately lobed, coarsely crenate to dentate to crenate to serrate; sinuses convergent and medium in depth to deep. Texture and luster, upper surface: Moderately to densely pubescent, not rugose; moderately velvety; slightly glossy. Texture and luster, lower surface: Moderately to densely pubescent, prominent venation; slightly velvety; matte. Venation pattern: Pinnate, reticulate. Color: Developing leaves, upper surface: Close to 137C. Developing leaves, lower surface: Close to 138B. Fully developed leaves, upper surface: Close to darker than 139A; venation, close to 147B. Fully developed leaves, lower surface: Close to 147B; venation, close to 148D. Petioles: Length: About 1.7 cm. Diameter: About 3 mm by 3.5 mm. Strength: Moderately strong. Texture and luster, upper and lower surfaces: Densely pubescent; slightly glossy. Color, upper surface: Close to 147C; edges, close to 137A. Color, lower surface: Close to 148D; edges, close to 138A. Stipules: Quantity, appearance and arrangement: Two leafy stipules, opposite, at the petiole attachment to the stem. Length: About 1.3 cm. Width: About 1.5 mm. Shape, in overall outline: Roughly reniform with emarginate apices. Texture and luster, upper surface: Moderately to densely pubescent; slightly glossy. Texture and luster, lower surface: Moderately to densely pubescent; matte. Color, upper surface: Close to darker than 139A. Color, lower surface: Close to 147B.

Inflorescence description:

*Appearance*.—Decorative-type inflorescence form with elliptic to ovate-shaped ray florets and tubular disc florets; inflorescences borne perpendicular to peduncles and face mostly upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 50 days later when grown as a disbud-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a spray-type, about 23 inflorescences develop per flowering stem.

*Inflorescence size*.—Diameter, grown as a spray-type: About 6.5 cm. Depth (height), grown as a spray-type: About 2.7 cm. Disc diameter, grown as a spray-type: About 2 mm; inconspicuous.

*Receptacles*.—Height: About 4 mm. Diameter: About 8 mm. Shape: Flattened globular. Color: Close to 145B to 145C.

*Inflorescence buds*.—Height: About 1.8 cm. Diameter: About 1.9 cm. Shape: Flattened spherical. Texture and luster: Distally, smooth and glabrous; proximally, moderately pubescent; slightly glossy. Color: Developing involucral bracts, close to 137B and 138A; developing ray florets, close to 70A and 70B and distally, close to 61A.

*Ray florets*.—Quantity and arrangement: About 200 arranged in about nine whorls. Length: About 2 cm; varying between 0.9 cm and 2.8 cm. Width: About 7 mm; varying between 0.1 cm and 1.2 cm. Shape: Elliptic to ovate; slightly concave, slightly carinate. Apex: Obtuse to emarginate. Base: Cuneate. Margin: Entire; coarsely undulate. Aspect: Erect to about 90° from vertical. Texture and luster, upper and lower surfaces: Smooth, glabrous; slightly velvety; matte. Color: When opening, upper and lower surfaces: Close to 72A; towards the base, close to 73D and at the base, close to 145B. Fully opened, upper surface: Close to NN155C; fine apical margin, close to 72B and at the base, close to 145A; venation, similar to lamina colors; colors do not change with subsequent development. Fully opened, lower surface: Close to NN155D; fine apical margin, close to N74C and at the base, close to 145A; venation, similar to lamina colors; with subsequent development, close to NN155D; towards the margins, slightly tinged with close to 75D; towards the apex, close to 72B and at the base, close to 145A.

*Disc florets*.—Quantity and arrangement: About five at the center of the receptacle. Length: About 5 mm. Diameter: About 1.25 mm. Shape: Lower 80% fused into a tube; upper 20% free. Apex: Narrowly acute. Margin, free-part: Entire. Texture and luster, inner and outer surfaces: Smooth, glabrous; glossy. Color, inner and outer surfaces: Apex: Close to N144C. Distally: Close to 11A. Proximally: Close to 145D.

*Involucral bracts*.—Quantity and arrangement: About 26 arranged in about two whorls. Length: About 1 cm. Width: About 4 mm. Shape: Narrowly ovate. Apex: Narrowly obtuse. Base: Cuneate. Margin: Entire. Texture and luster, upper surface: Smooth, glabrous; glossy. Texture and luster, lower surface: Moderately pubescent; matte. Color, upper surface: Close to 146A to 146B; lateral margins, translucent and close to 156C to 156D and apical margins tinged with close to N199A. Color, lower surface: Close to NN137B; lateral margins, translucent and close to 156C to 156D and apical margins tinged with close to N199A.

*Peduncles*.—Length, terminal peduncle: About 3.7 cm. Diameter, terminal peduncle: About 3.5 mm. Length, third peduncle: About 8.8 cm. Diameter, third peduncle: About 3 mm. Strength: Strong. Aspect, terminal peduncle: Upright. Aspect, third peduncle: About 50° from the flowering stem axis. Texture and luster: Moderately pubescent; slightly glossy. Color: Close to 137B and 138A.

*Reproductive organs*.—Androecium: Present on disc florets only. Quantity: About five per floret. Filament length: About 2 mm. Filament color: Close to 145C to 145D. Anther size: About 0.5 mm by 2 mm.

Anther shape: Oblong. Anther color: Close to 14A. Pollen amount: Moderate. Pollen color: Close to 17A. Gynoecium: Present on both ray and disc florets. Quantity: One per floret. Pistil length: About 6.5 mm. Style length: About 5.5 mm. Style color: Close to 145D. Stigma diameter: About 1 mm. Stigma shape: Cleft to three-parted, decurrent. Stigma color: Close to 12A. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* (*Fusarium oxysporum*). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFSHOR12' as illustrated and described.

* * * * *